(12) United States Patent
Mizuguchi

(10) Patent No.: US 9,839,520 B2
(45) Date of Patent: Dec. 12, 2017

(54) ARTIFICIAL KNEE JOINT IMPLANT

(71) Applicant: KYOCERA Medical Corporation, Osaka-shi, Osaka (JP)

(72) Inventor: Tomoyuki Mizuguchi, Osaka (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 65 days.

(21) Appl. No.: 14/900,379

(22) PCT Filed: Jun. 26, 2014

(86) PCT No.: PCT/JP2014/067044
§ 371 (c)(1),
(2) Date: Dec. 21, 2015

(87) PCT Pub. No.: WO2014/208687
PCT Pub. Date: Dec. 31, 2014

(65) Prior Publication Data
US 2016/0158020 A1 Jun. 9, 2016

(30) Foreign Application Priority Data

Jun. 27, 2013 (JP) .................................. 2013-134777

(51) Int. Cl.
*A61F 2/38* (2006.01)
*A61F 2/30* (2006.01)

(52) U.S. Cl.
CPC .............. *A61F 2/3836* (2013.01); *A61F 2/38* (2013.01); *A61F 2/389* (2013.01); *A61F 2/3859* (2013.01); *A61F 2002/30607* (2013.01)

(58) Field of Classification Search
CPC ...... A61F 2/389; A61F 2/3868; A61F 2/3859; A61F 2/38; A61F 2220/0025; A61F 2/3836
See application file for complete search history.

(56) References Cited

U.S. PATENT DOCUMENTS

| 5,080,675 | A   |   | 1/1992  | Lawes et al. |
|-----------|-----|---|---------|--------------|
| 5,702,464 | A   | * | 12/1997 | Lackey ............... A61F 2/4684 |
|           |     |   |         | 623/20.32    |
| 8,414,653 | B2  |   | 4/2013  | Burstein et al. |
| 8,496,704 | B2  |   | 7/2013  | Lenz et al.  |

(Continued)

FOREIGN PATENT DOCUMENTS

| CN | 101431968 A | 5/2009 |
| CN | 101708138 A | 5/2010 |

(Continued)

OTHER PUBLICATIONS

Extended European Search Report, European Patent Application No. 14817806.4, dated Jan. 17, 2017, 7 pgs.

(Continued)

*Primary Examiner* — Jason-Dennis Stewart
(74) *Attorney, Agent, or Firm* — Volpe and Koenig, P.C.

(57) ABSTRACT

Provided is an artificial knee joint implant with which the balance between ligaments can be properly adjusted. An artificial knee joint implant includes a plurality of types of tibial plates-having tibia-side sliding faces that slide against femoral components and respectively having at least either the tibia-side sliding faces at different positions with respect to a tibia in a state where the tibial plates are fixed to a tibial tray attached to a tibia, or the tibia-side sliding faces in different shapes.

7 Claims, 12 Drawing Sheets

(56) References Cited

U.S. PATENT DOCUMENTS

| | | |
|---|---|---|
| 9,233,002 B2 | 1/2016 | Lenz et al. |
| 2002/0156535 A1 | 10/2002 | Pappas |
| 2005/0197709 A1 | 9/2005 | Schaefer et al. |
| 2007/0100463 A1 | 5/2007 | Aram et al. |
| 2008/0058945 A1 | 3/2008 | Hajaj et al. |
| 2008/0140212 A1 | 6/2008 | Metzger et al. |
| 2009/0204222 A1 | 8/2009 | Burstein et al. |
| 2011/0029091 A1* | 2/2011 | Bojarski ............ A61F 2/30942 623/20.32 |
| 2011/0178606 A1 | 7/2011 | Deffenbaugh et al. |
| 2011/0251695 A1 | 10/2011 | Lenz et al. |
| 2011/0313534 A1* | 12/2011 | Ries ................ A61F 2/3868 623/20.27 |
| 2012/0078263 A1 | 3/2012 | Parisi et al. |
| 2013/0060344 A1* | 3/2013 | Pierce ................ A61F 2/3859 623/20.28 |
| 2013/0226305 A1* | 8/2013 | Donno ............... A61F 2/3859 623/20.35 |
| 2013/0317620 A1 | 11/2013 | Lenz et al. |
| 2014/0243989 A1 | 8/2014 | Nabeshima et al. |

FOREIGN PATENT DOCUMENTS

| | | |
|---|---|---|
| CN | 101977570 A | 2/2011 |
| CN | 102133137 A | 7/2011 |
| CN | 102283724 A | 12/2011 |
| EP | 1974694 A1 | 10/2008 |
| JP | 2004-166802 A | 6/2004 |
| JP | 2009-513275 A | 4/2009 |
| JP | 2009-529956 A | 8/2009 |
| JP | 2013-070738 A | 4/2013 |
| WO | 99/34755 A1 | 7/1999 |
| WO | 2011/130208 A2 | 10/2011 |

OTHER PUBLICATIONS

International Search Report, PCT/JP2014/067044, dated Sep. 16, 2014, 2 pgs.

Chinese Office Action with English concise explanation and machine translation, Chinese Patent Application No. 01480036638.9, dated Aug. 1, 2016, 24 pgs.

\* cited by examiner

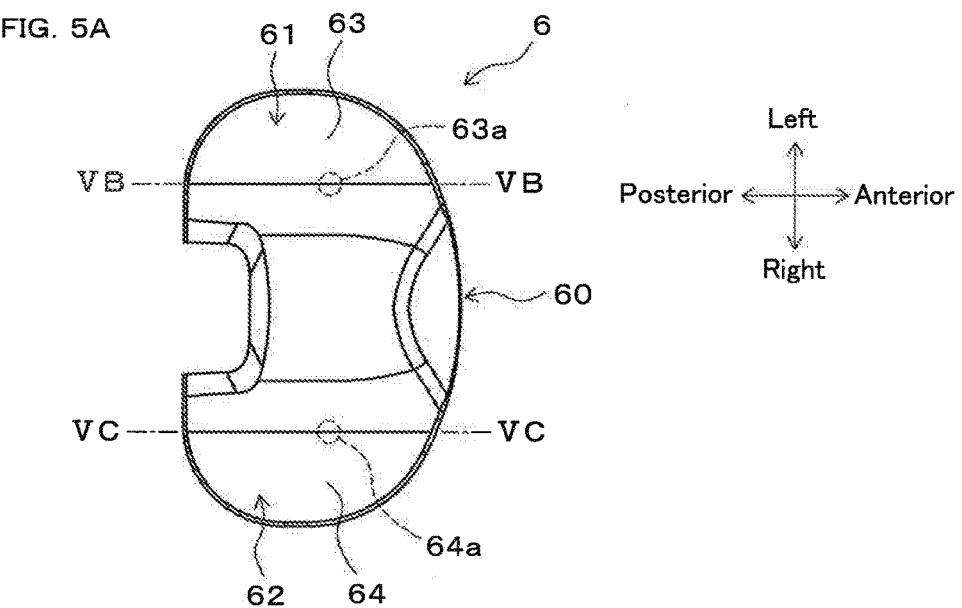
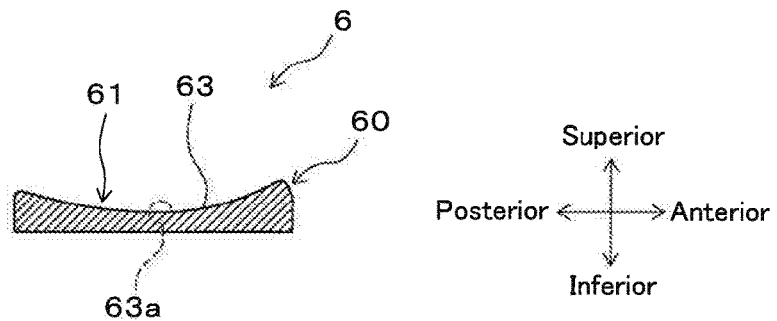
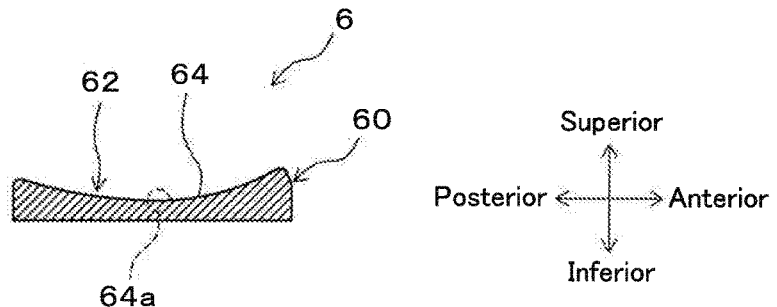

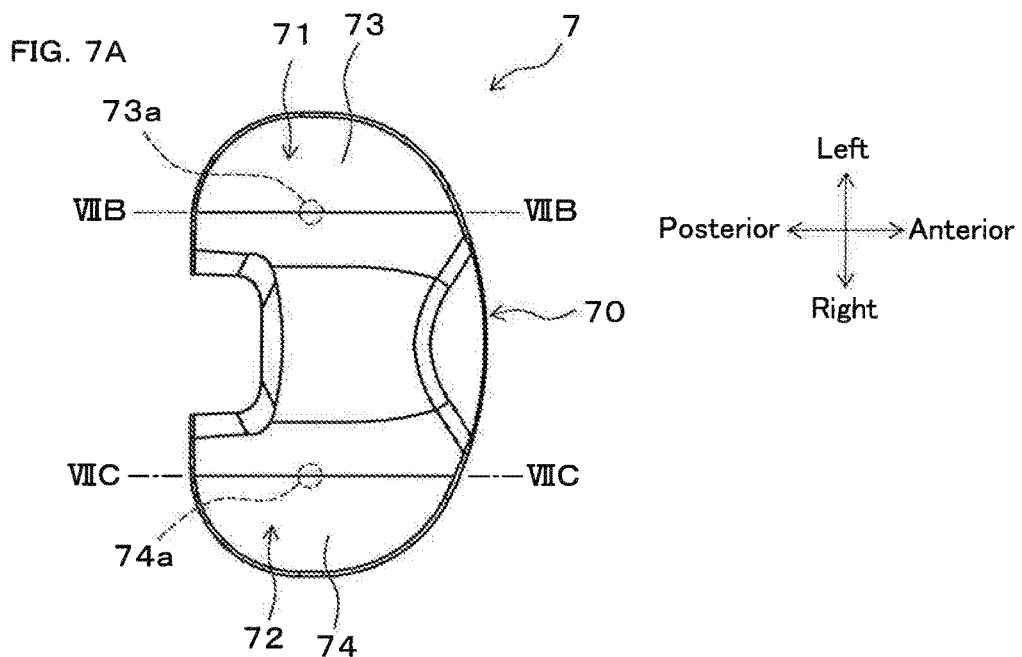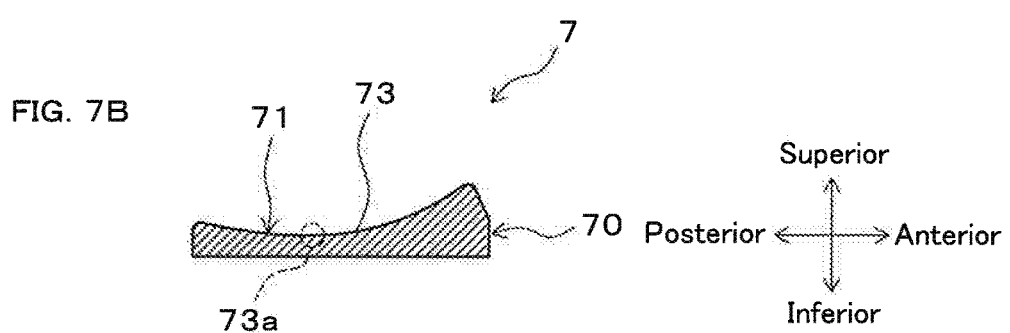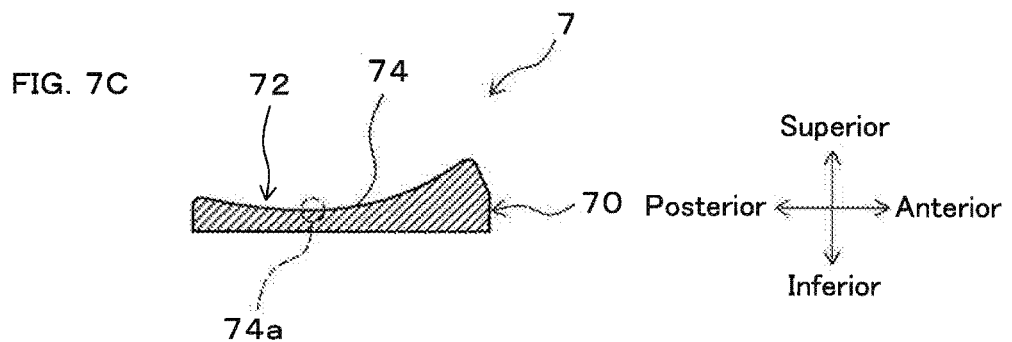

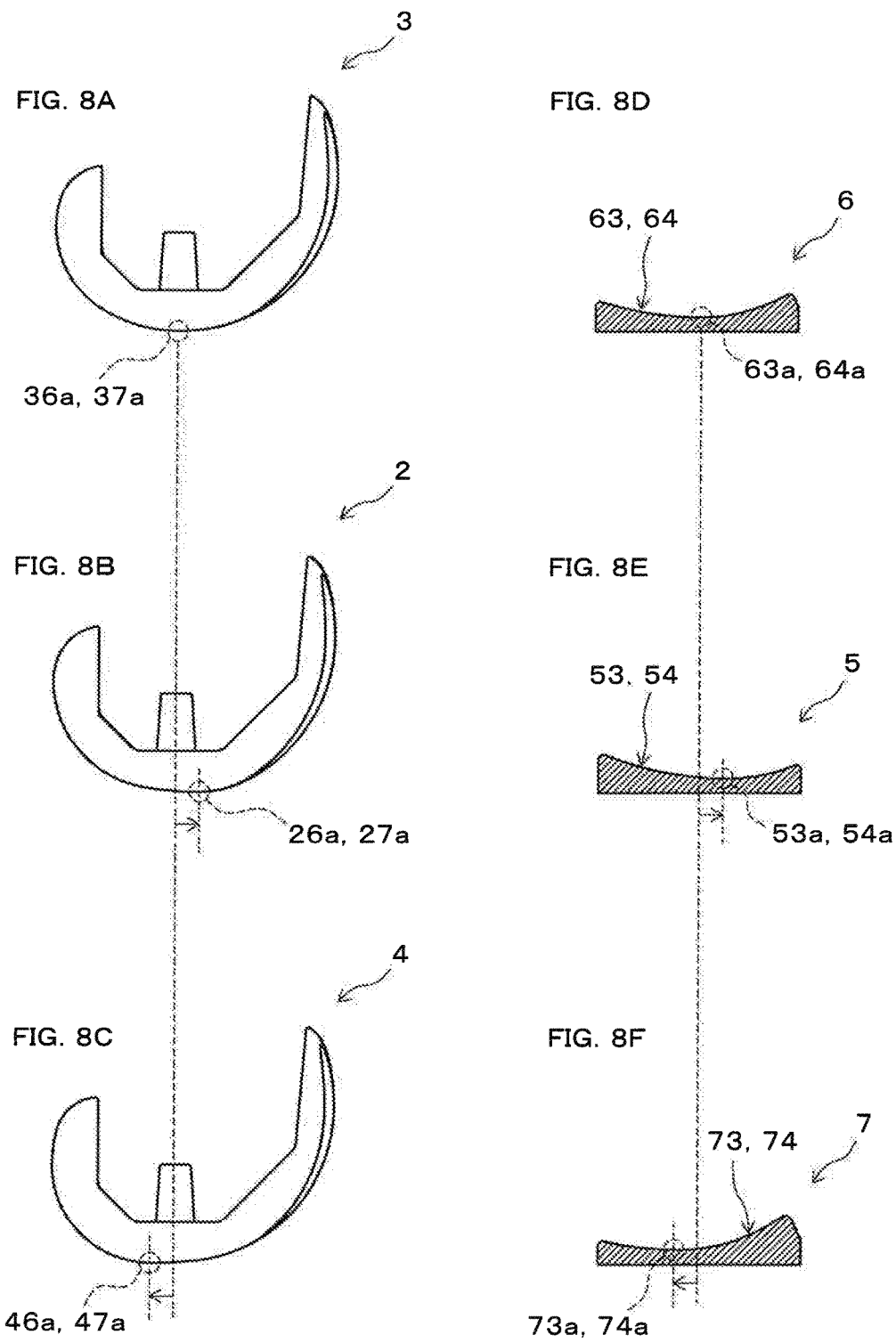

Most inferior points of anterior-type femoral component

Most inferior points of standard-type femoral component

Most inferior points of posterior-type femoral component

Most inferior points of anterior-type tibial component

Most inferior points of standard-type tibial component

Most inferior points of posterior-type tibial component

ARTIFICIAL KNEE JOINT IMPLANT

CROSS-REFERENCE TO RELATED APPLICATION

This application is a U.S. National Stage entry of PCT Application No. PCT/JP2014/067044, filed Jun. 26, 2014, which claims the benefit of priority from Japanese patent application No. 2013-134777, filed on Jun. 27, 2013, the disclosures of which are herein incorporated by reference in its entirety.

BACKGROUND OF THE INVENTION

1. Field of the Invention

The present invention relates to an artificial knee joint implant including a femoral component and a tibial plate.

2. Description of Related Art

Conventionally, for example, as disclosed in JP 2004-166802A, there is a known artificial knee joint including a femoral component that is fixed to a distal end of a femur and a tibial component (tibial plate) that is fixed to a proximal end of a tibia. This artificial knee joint is configured such that its medial pivot angle changes in accordance with a change in the flexion angle of the artificial knee joint.

SUMMARY OF THE INVENTION

Typically, the femoral component and the tibial plate are positioned so as to maintain the balance between medial collateral ligament tension and lateral collateral ligament tension. However, if a contact position of the artificial knee joint is not properly set, the balance between both collateral ligaments may be poor, thus incurring a heavy burden on the patient's knee.

The present invention solves the above-described problem, and it is an object thereof to provide an artificial knee joint implant with which the balance between ligaments can be properly adjusted.

(1) In order to achieve the above-described object, an aspect of the present invention is directed to an artificial knee joint implant, including a femoral component and a tibial plate, wherein the tibial plate has a tibia-side sliding face that slides against the femoral component, and the artificial knee joint implant includes a plurality of types of said tibial plates respectively having at least either the tibia-side sliding faces at different positions with respect to a tibia in a state where the tibial plates are fixed to a tibial tray attached to the tibia, or the tibia-side sliding faces in different shapes.

With this configuration, a surgeon can select one of a plurality of types of tibial plates according to the shape, the condition, and the like of a knee joint of a patient, and attach that tibial plate to the patient's knee. Accordingly, the contact position of the femoral component and the tibial plate can be adjusted, and, thus, a proper balance between both collateral ligaments can be easily realized.

Accordingly, with this configuration, it is possible to provide an artificial knee joint implant with which the balance between ligaments can be properly adjusted.

(2) It is preferable that the tibia-side sliding faces are respectively provided with distalmost points positioned on a distalmost side in an extension direction, which is a direction in which the artificial knee joint implant is fixed to a femur and the tibia is extended, and each of the plurality of types of tibial plates has the distalmost point whose position with respect to a knee joint is different from the positions of the distalmost points of the other tibial plates in an anterior-posterior direction in a state where the tibial plates are fixed to the tibial tray.

If a plurality of types of tibial plates respectively having distalmost points at different positions in the anterior-posterior direction are formed as in this configuration, the contact position of the femoral component and the tibial plate in the anterior-posterior direction can be adjusted relatively easily.

(3) It is more preferable that the distalmost points include a first distalmost point, a second distalmost point, and a third distalmost point respectively corresponding to the plurality of types of tibial plates, and the plurality of tibial plates include a first tibial plate provided with the first distalmost point that is at a predetermined position in the anterior-posterior direction, a second tibial plate provided with the second distalmost point that is closer to an anterior side than the first distalmost point is in the anterior-posterior direction, and a third tibial plate provided with the third distalmost point that is closer to a posterior side than the first distalmost point is in the anterior-posterior direction.

With this configuration, for example, first to third tibial plates can be formed in which the position of the distalmost point that realizes the most proper balance between ligaments of an average patient undergoing artificial knee joint replacement surgery is set to a first distalmost point, on the anterior side and the posterior side of which a second distalmost point and a third distalmost point are set. With this configuration, it is possible to provide an artificial knee joint implant with which the balance between ligaments can be properly adjusted for more patients.

(4) It is more preferable that the first tibial plate is provided with a first medial-side distalmost point and a first lateral-side distalmost point as two first distalmost points that are spaced away from each other in a left-right direction, the second tibial plate is provided with a second medial-side distalmost point and a second lateral-side distalmost point as two second distalmost points that are spaced away from each other in the left-right direction, the third tibial plate is provided with a third medial-side distalmost point and a third lateral-side distalmost point as two third distalmost points that are spaced away from each other in the left-right direction, and separation intervals of the medial-side distalmost points in the anterior-posterior direction and separation intervals of the lateral-side distalmost points in the anterior-posterior direction are different from each other.

With this configuration, the separation intervals of the first to third medial-side distalmost points in the anterior-posterior direction and the separation intervals of the first to third lateral-side distalmost points in the anterior-posterior direction can be properly set independently, and, thus, it is possible to provide an artificial knee joint implant that fits more patients.

(5) In order to achieve the above-described object, an aspect of the present invention is directed to an artificial knee joint implant, including a femoral component and a tibial plate, wherein the femoral component has a femur-side sliding face that slides over the tibial plate, and the artificial knee joint implant includes a plurality of types of said femoral components respectively having at least either the femur-side sliding faces at different positions with respect to a femur in a state where the femoral components are fixed to the femur, or the femur-side sliding faces in different shapes.

With this configuration, a surgeon can select one of a plurality of types of femoral components according to the shape, the condition, and the like of a knee joint of a patient, and attach that femoral component to the patient's knee. Accordingly, the contact position of the femoral component and the tibial plate can be adjusted, and, thus, a proper balance between both collateral ligaments can be easily realized.

Accordingly, with this configuration, it is possible to provide an artificial knee joint implant with which the balance between ligaments can be properly adjusted.

(6) It is preferable that the femur-side sliding faces are respectively provided with distalmost points positioned on a distalmost side in an extension direction, which is a direction in which the artificial knee joint implant that is fixed to the femur and a tibia is extended, and each of the plurality of types of femoral components has the distalmost point whose position with respect to a knee joint is different from the positions of the distalmost points of the other femoral components in an anterior-posterior direction in a state where the femoral components are fixed to the femur.

If a plurality of types of femoral components respectively having distalmost points at different positions in the anterior-posterior direction are formed as in this configuration, the contact position of the femoral component and the tibial plate in the anterior-posterior direction can be adjusted relatively easily.

(7) It is more preferable that the distalmost points include a first distalmost point, a second distalmost point, and a third distalmost point respectively corresponding to the plurality of types of femoral components, and the plurality of femoral components include a first femoral component provided with the first distalmost point that is at a predetermined position in the anterior-posterior direction, a second femoral component provided with the second distalmost point that is closer to an anterior side than the first distalmost point is in the anterior-posterior direction, and a third femoral component provided with the third distalmost point that is closer to a posterior side than the first distalmost point is in the anterior-posterior direction.

With this configuration, for example, first to third femoral components can be formed in which the position of the distalmost point that realizes the most proper balance between ligaments of an average patient undergoing artificial knee joint replacement surgery is set to a first distalmost point, on the anterior side and the posterior side of which a second distalmost point and a third distalmost point are set. With this configuration, it is possible to provide an artificial knee joint implant with which the balance between ligaments can be properly adjusted for more patients.

(8) It is more preferable that the first femoral component is provided with a first medial-side distalmost point and a first lateral-side distalmost point as two first distalmost points that are spaced away from each other in a left-right direction, the second femoral component is provided with a second medial-side distalmost point and a second lateral-side distalmost point as two second distalmost points that are spaced away from each other in the left-right direction, the third femoral component is provided with a third medial-side distalmost point and a third lateral-side distalmost point as two third distalmost points that are spaced away from each other in the left-right direction, and separation intervals of the medial-side distalmost points in the anterior-posterior direction and separation intervals of the lateral-side distalmost points in the anterior-posterior direction are different from each other.

With this configuration, the separation intervals of the first to third medial-side distalmost points in the anterior-posterior direction and the separation intervals of the first to third lateral-side distalmost points in the anterior-posterior direction can be properly set independently, and, thus, it is possible to provide an artificial knee joint implant that fits more patients.

BRIEF DESCRIPTION OF DRAWINGS

FIG. 2A shows view of a most inferior point standard-type femoral component, wherein FIG. 2A is a side view thereof.

FIG. 2B shows view of a most inferior point standard-type femoral component, wherein FIG. 2B is a bottom view thereof.

FIG. 3A shows view of a most inferior point anterior-type femoral component, wherein FIG. 3A is a side view thereof.

FIG. 3B shows view of a most inferior point anterior-type femoral component, wherein FIG. 3B is a bottom view thereof.

FIG. 4A shows view of a most inferior point posterior-type femoral component, wherein FIG. 4A is a side view thereof.

FIG. 4B shows view of a most inferior point posterior-type femoral component, wherein FIG. 4B is a bottom view thereof.

FIG. 5A shows view of a most inferior point standard-type tibial plate, wherein FIG. 5A is a plan view thereof.

FIG. 5B shows view of a most inferior point standard-type tibial plate, wherein FIG. 5B is a cross-sectional view taken along the line VB-VB in FIG. 5A.

FIG. 5C shows view of a most inferior point standard-type tibial plate, wherein FIG. 5C is a cross-sectional view taken along the line VC-VC in FIG. 5A.

FIG. 6A shows view of a most inferior point anterior-type tibial plate, wherein FIG. 6A is a plan view thereof.

FIG. 6B shows view of a most inferior point anterior-type tibial plate, wherein FIG. 6B is a cross-sectional view taken along the line VIB-VIB in FIG. 6A.

FIG. 6C shows view of a most inferior point anterior-type tibial plate, wherein FIG. 6C is a cross-sectional view taken along the line VIC-VIC in FIG. 6A.

FIG. 7A shows view of a most inferior point posterior-type tibial plate, wherein FIG. 7A is a plan view thereof.

FIG. 7B shows view of a most inferior point posterior-type tibial plate, wherein FIG. 7B is a cross-sectional view taken along the line VIIB-VIIB in FIG. 7A.

FIG. 7C shows view of a most inferior point posterior-type tibial plate, wherein FIG. 7C is a cross-sectional view taken along the line VIIC-VIIC in FIG. 7A.

FIGS. 8A to 8C show views illustrating a difference in an anterior-posterior direction between most inferior points respectively provided on a plurality of types of femoral components, and FIGS. 8D to 8F show views illustrating a difference in the anterior-posterior direction between most inferior points respectively provided on a plurality of types of tibial plates.

FIG. 9A shows view of a state in which a femoral component and a tibial plate are attached to a patient's knee, wherein FIG. 9A is a view showing a combination of a standard-type femoral component and a standard-type tibial plate.

FIG. 9B shows view of a state in which a femoral component and a tibial plate are attached to a patient's knee, wherein FIG. 9B is a view showing a combination of a standard-type femoral component and an anterior-type tibial plate.

FIG. 9C shows view of a state in which a femoral component and a tibial plate are attached to a patient's knee, wherein FIG. 9C is a view showing a combination of a standard-type femoral component and a posterior-type tibial plate.

FIG. 12A to 12F show views illustrating shapes of an artificial knee joint implant (PS-type) according to a modified example, wherein FIGS. 12A to 12C are side views respectively showing a plurality of types of femoral components, and FIGS. 12D to 12F are plan views respectively showing a plurality of types of tibial plates.

DETAILED DESCRIPTION OF THE INVENTION

Hereinafter, an embodiment for carrying out the present invention will be described with reference to the drawings. The present invention is widely applicable as an artificial knee joint implant including a femoral component and a tibial plate.

Figure 1:
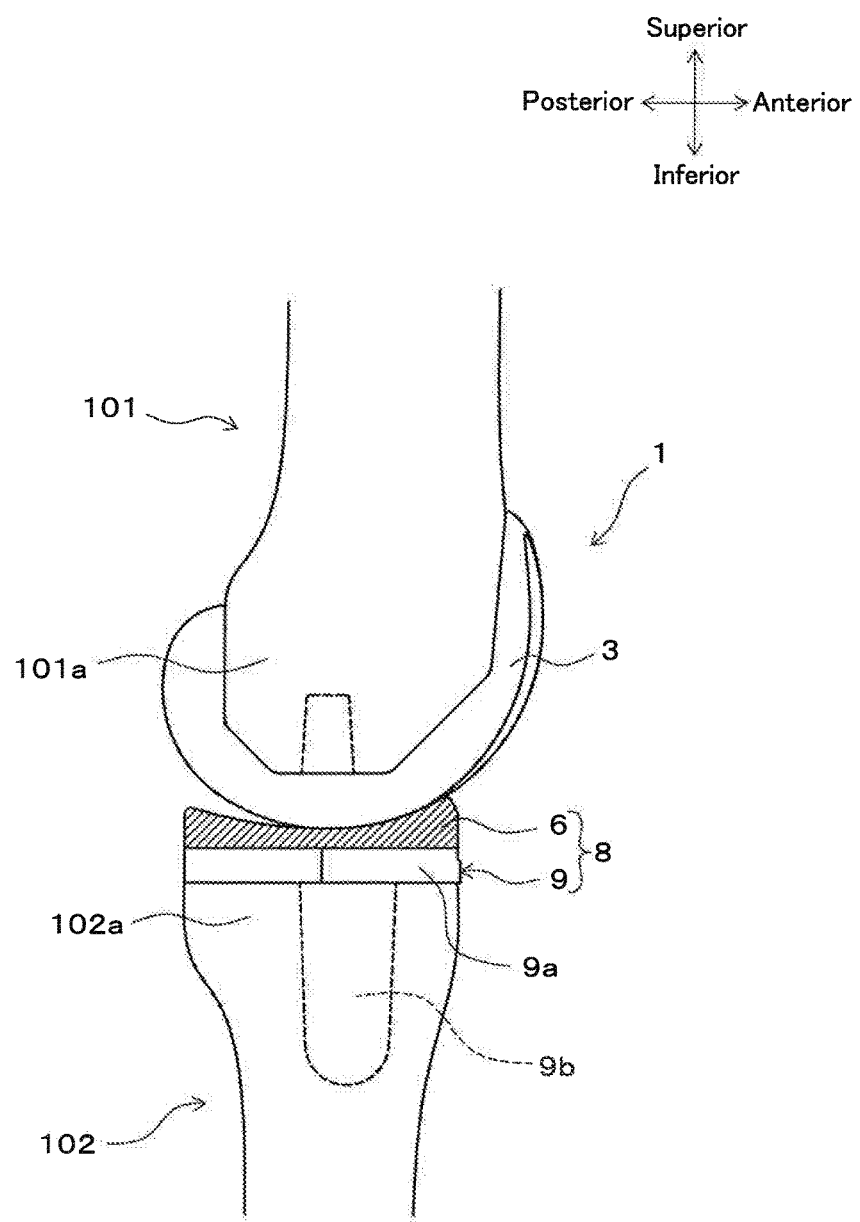
FIG. 1 shows a partial cross-sectional view showing an example of an artificial knee joint implant in a state of use according to an embodiment, in a state of being attached to a femur and a tibia of patient.

FIG. 1 shows a partial cross-sectional view showing an example of a an artificial knee joint implant 1 in a state of use according to an embodiment of the present invention, in a state of being attached to a femur 101 and a tibia 102 of a patient, viewed from a side of the patient. The artificial knee joint implant 1 is used in surgery for replacing a knee joint of a patient with an artificial knee joint. The artificial knee joint implant 1 is used, for example, to recover normal functions of a patient's knee in which the knee joint has been highly deformed due to osteoarthritis, chronic rheumatoid arthritis, or the like. The artificial knee joint implant 1 according to this embodiment is used in cruciate retaining (CR)-type artificial knee joint replacement surgery for replacing a knee joint of a patient with an artificial knee joint in a state where an anterior cruciate ligament of the patient has been removed but a posterior cruciate ligament is retained.

As shown in FIG. 1, the artificial knee joint implant 1 includes a femoral component 3 and a tibial component 8. The femoral component 3 is fixed to a distal end 101a of the femur 101.

The tibial component 8 includes a tibial tray 9 and a tibial plate 6. The tibial tray 9 has a flat plate portion 9a formed in the shape of a flat plate and a projecting portion 9b projecting to the inferior side from the flat plate portion 9a, both of which are formed in one piece. The tibial tray 9 is fixed to the tibia 102 by allowing the projecting portion 9b to be inserted into and fixed to a hole portion 102b formed at a proximal end 102a of the tibia 102. The tibial plate 6 is fixed to a superior face of the flat plate portion 9a of the tibial tray 9 fixed to the tibia 102. Accordingly, the tibial plate 6 is fixed to the tibia 102. The femoral component shown in FIG. 1 is a most inferior point standard-type femoral component 3, and the tibial plate 6 shown in FIG. 1 is a most inferior point standard-type tibial plate 6 (described later in detail).

The artificial knee joint implant 1 according to this embodiment includes a plurality of types (three types, in this embodiment) of femoral components and a plurality of types (three types, in this embodiment) of tibial plates. Specifically, the artificial knee joint implant 1 includes, as the femoral components, the most inferior point standard-type femoral component 3 (first femoral component), a most inferior point anterior-type femoral component 2 (second femoral component), and a most inferior point posterior-type femoral component 4 (third femoral component). Furthermore, the artificial knee joint implant 1 includes, as the tibial plates, the most inferior point standard-type tibial plate 6 (first tibial plate), a most inferior point anterior-type tibial plate 5 (second tibial plate), and a most inferior point posterior-type tibial plate 7 (third tibial plate).

Figure 2A:
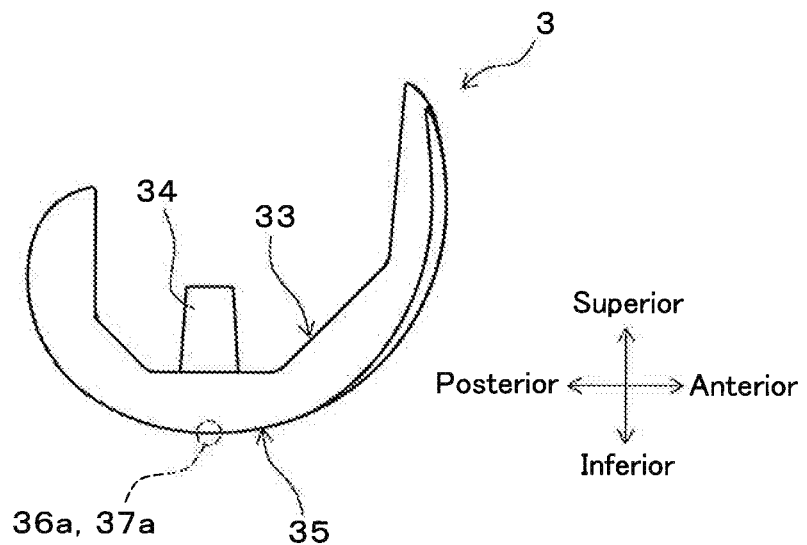
Figure 2B:
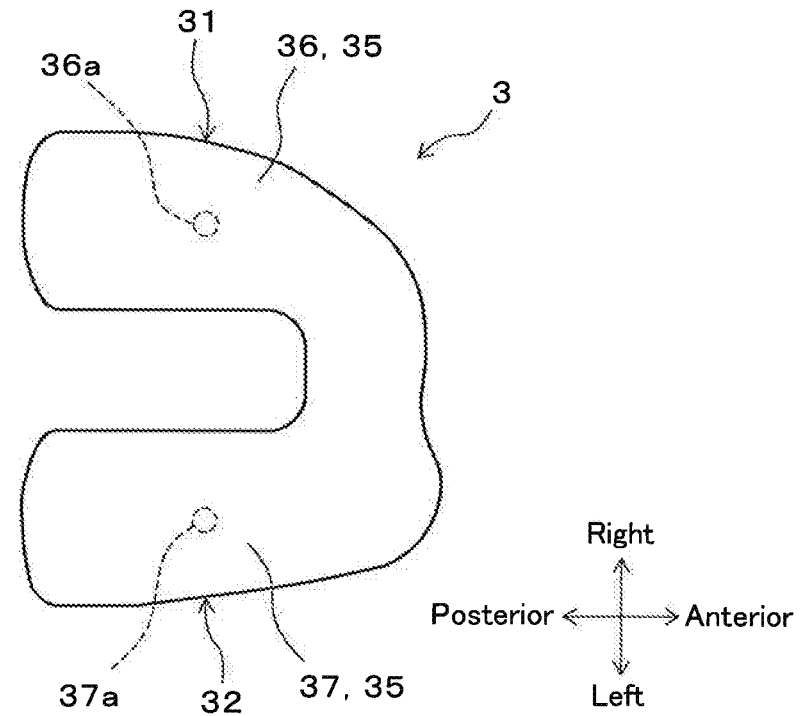
Figure 3A:
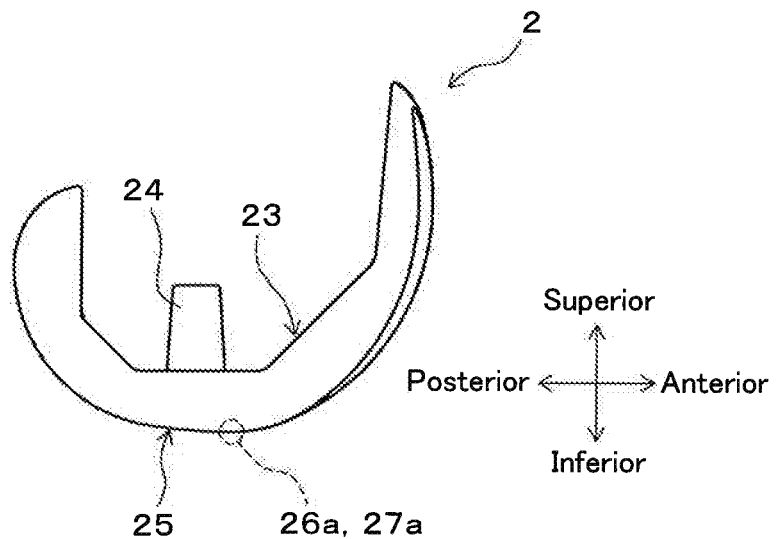
Figure 3B:
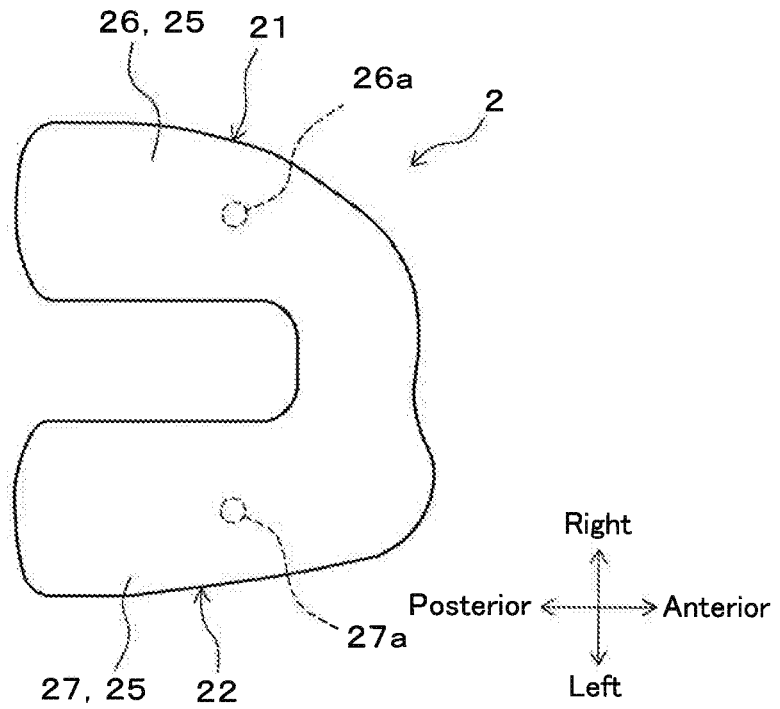
Figure 4A:
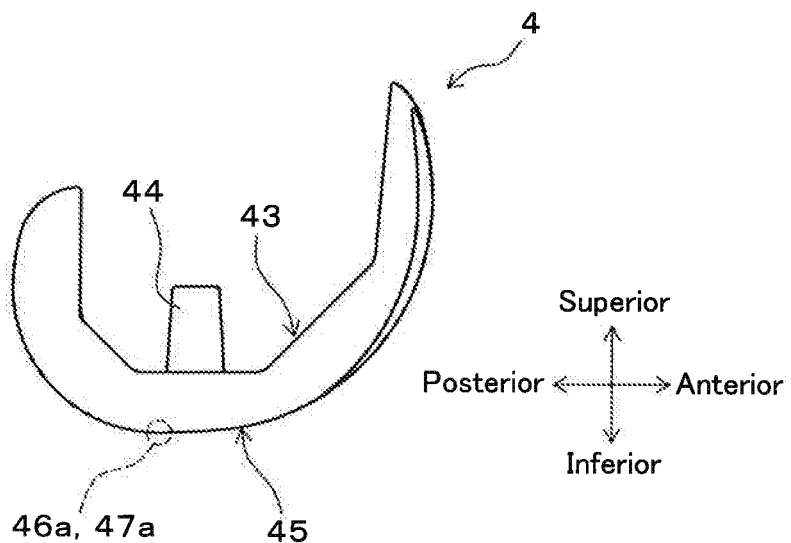
Figure 4B:
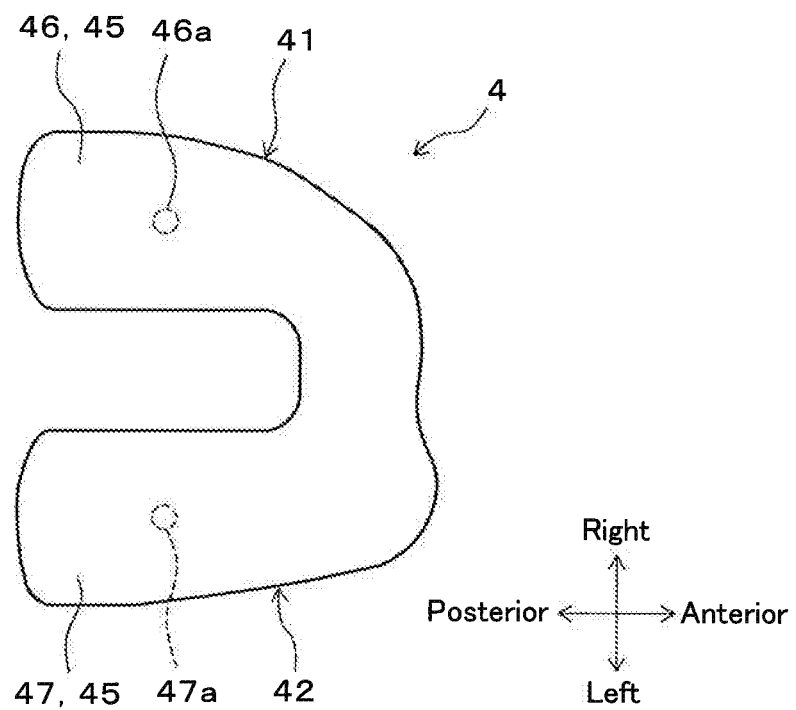
Figure 6A:
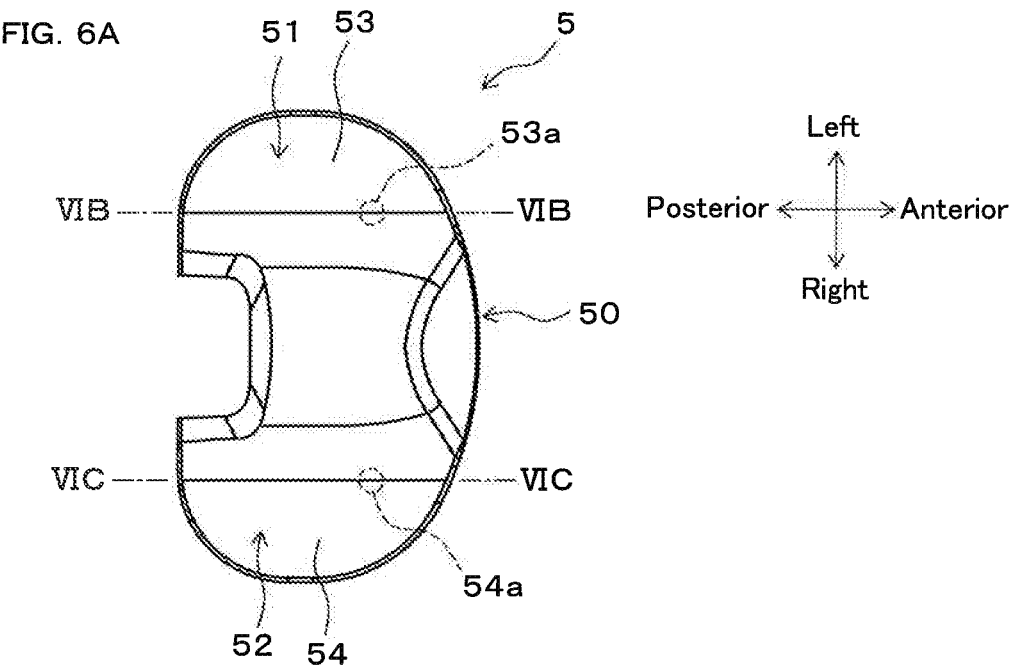
Figure 6B:
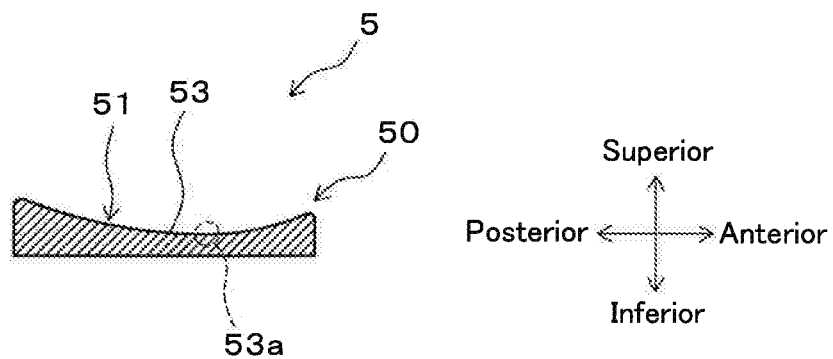
Figure 6C:
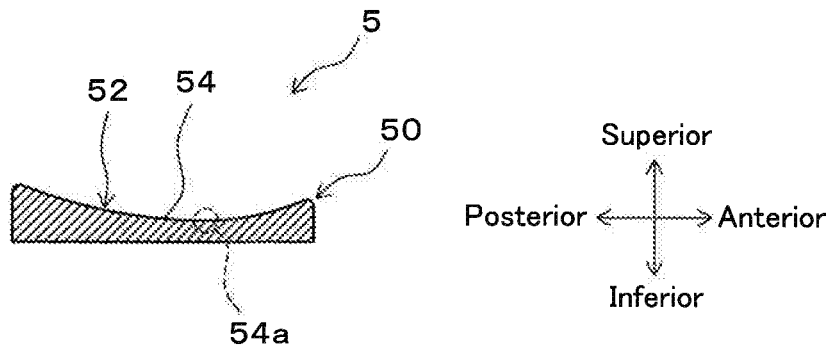

FIGS. 2 to 4 are views respectively showing the most inferior point standard-type femoral component 3, the most inferior point anterior-type femoral component 2, and the most inferior point posterior-type femoral component 4, wherein FIGS. 2A, 3 A, and 4 A are side views thereof, and FIGS. 2B, 3 B, and 4 B are bottom views thereof. Furthermore, FIGS. 5 to 7 are views respectively showing the most inferior point standard-type tibial plate 6, the most inferior point anterior-type tibial plate 5, and the most inferior point posterior-type tibial plate 7, wherein FIGS. 5 A, 6 A, and 7 A are plan views thereof, and FIGS. 5B, 5C, 6B, 6C, 7B, and 7C are cross-sectional views thereof.

In FIGS. 2 to 7, for the sake of ease of description, it is assumed that the direction indicated by the arrow "anterior" is referred to as an anterior side or an anterior direction, the direction indicated by the arrow "posterior" is referred to as a posterior side or a posterior direction, the direction indicated by the arrow "superior" is referred to as a superior side or a superior direction, the direction indicated by the arrow "inferior" is referred to as an inferior side or an inferior direction, the direction indicated by the arrow "right" is referred to as a right side, and the direction indicated by the arrow "left" is referred to as a left side. The anterior direction and the posterior direction in FIGS. 2 to 7 correspond to the anterior-posterior direction of a knee joint and a human body.

The femoral components 2, 3, and 4 are different from each other in their shapes, in particular, in their shapes of femur-side sliding faces that slide over the tibial plate. Specifically, the femoral components 2, 3, and 4 are significantly different from each other in that most inferior points (distalmost points) provided on their femur-side sliding faces are at different positions with respect to a knee joint in the anterior-posterior direction.

In a similar manner, the tibial plates 5, 6, and 7 are different from each other in their shapes, in particular, in the shapes of their tibia-side sliding faces that slide against the femoral component. Specifically, the tibial plates 5, 6, and 7 are significantly different from each other in that the most inferior points (distalmost points) provided on their tibia-side sliding faces are at different positions with respect to a knee joint in the anterior-posterior direction.

Note that the most inferior points (distalmost points) are points positioned on the distalmost side in a direction (extension direction) in which the artificial knee joint implant attached to the patient's knee is extended.

According to the artificial knee joint implant 1, one femoral component and one tibial plate are selected from among the plurality of types of femoral components 2, 3, and 4 and tibial plates 5, 6, and 7 according to the shape, the condition, and the like of a knee joint of a patient, and are attached to the patient's knee.

Configuration of Femoral Component

As described above, as the femoral components, there are three types of femoral components (the anterior-type femoral component 2, the standard-type femoral component 3, and the posterior-type femoral component 4). These three types of femoral components 2, 3, and 4 have substantially the same configuration except for the positions of the most inferior points in the anterior-posterior direction. Thus, in the description below, the configuration of the standard-type femoral component 3 will be described first. Subsequently, the configurations of the anterior-type and posterior-type femoral components 2 and 4 will be described mainly focusing on aspects of the configurations different from those of the standard-type femoral component 3.

The standard-type femoral component 3 is made of, for example, a metal material having high biocompatibility. As shown in FIGS. 2A and 2B, the standard-type femoral component 3 has a substantial U-shape when viewed both from a side and from below.

The standard-type femoral component 3 includes a medial condyle 31 and a lateral condyle 32. The medial condyle 31 and the lateral condyle 32 are arranged side by side in the left-right direction. The anterior portion of the medial condyle 31 and the anterior portion of the lateral condyle 32 are connected to each other. The intermediate portion and the posterior portion of the medial condyle 31 and the intermediate portion and the posterior portion of the lateral condyle 32 are spaced away from each other in the left-right direction, and are arranged approximately parallel to each other in the anterior-posterior direction.

The standard-type femoral component 3 is provided with, on an inner face thereof facing the distal end 101a of the femur 101, a fixing face 33. The fixing face 33 is provided in order to fix the femoral component 3 to the distal end 101a of the femur 101. The fixing face 33 is provided with a projecting portion 34 projecting from the fixing face 33. The fixing face 33 is fixed to the distal end 101a in a state where the projecting portion 34 is inserted into a hole formed at the distal end 101a of the femur 101.

Furthermore, the standard-type femoral component 3 is provided with, on an outer circumferential face thereof facing the side opposite from the distal end 101a of the femur 101, femur-side sliding faces 35. The femur-side sliding faces 35 include a femur-medial-side sliding face 36 on the medial condyle 31 and a femur-lateral-side sliding face 37 on the lateral condyle 32. The femur-medial-side sliding face 36 and the femur-lateral-side sliding face 37 are in the shape of a curved face projecting toward the side opposite from the distal end 101a.

Peak points of the sliding faces 36 and 37 projecting as described above are provided as most inferior points 36a and 37a (first distalmost points). The most inferior point 36a provided on the medial-side sliding face 36 is provided as the first medial-side most inferior point 36a, and the most inferior point 37a provided on the lateral-side sliding face 37 is provided as the first lateral-side most inferior point 37a. The first medial-side most inferior point 36a and the first lateral-side most inferior point 37a are positioned on the distalmost side in a state where the artificial knee joint implant 1 attached to a patient is extended. The most inferior points 36a and 37a are formed at substantially the same position as the position at which the projecting portion 34 is formed, in the anterior-posterior direction, in the standard-type femoral component 3 when viewed from a side.

The anterior-posterior positions of the most inferior points provided on the anterior-type femoral component 2 and the posterior-type femoral component 4 are different from those of the most inferior points provided on the standard-type femoral component 3 in the anterior-posterior direction. The other portions have substantially the same shapes.

As shown in FIG. 3, the anterior-type femoral component 2 also has a medial-side most inferior point 26a (second distalmost point) provided on a femur-medial-side sliding face 26 of a medial condyle 21 and a lateral-side most inferior point 27a (second distalmost point) provided on a femur-lateral-side sliding face 27 of a lateral condyle 22, as in the case of the standard-type femoral component 3. In the anterior-type femoral component 2, the medial-side most inferior point 26a is provided as the second medial-side most inferior point 26a, and the lateral-side most inferior point 27a is provided as the second lateral-side most inferior point 27a.

As shown in FIG. 3, the second medial-side most inferior point 26a and the second lateral-side most inferior point 27a are provided so as to be closer to the anterior side than the first medial-side most inferior point 36a and the first lateral-side most inferior point 37a provided on the standard-type femoral component 3 are in the anterior-posterior direction. For example, the second medial-side most inferior point 26a and the second lateral-side most inferior point 27a are provided so as to be closer to the anterior side by 1 mm than the first medial-side most inferior point 36a and the first lateral-side most inferior point 37a are. FIG. 3 shows, in an exaggerated manner, the amount of difference of the most inferior points 26a and 27a of the anterior-type femoral component in the anterior-posterior direction, from the most inferior points 36a and 37a of the standard-type femoral component 3.

On the other hand, as shown in FIG. 4, the posterior-type femoral component 4 also has a medial-side most inferior point 46a (third distalmost point) provided on a femur-medial-side sliding face 46 of a medial condyle 41 and a lateral-side most inferior point 47a (third distalmost point) provided on a femur-lateral-side sliding face 47 of a lateral condyle 42, as in the case of the standard-type femoral component 3. In the posterior-type femoral component 4, the medial-side most inferior point 46a is provided as the third medial-side most inferior point 46a, and the lateral-side most inferior point 47a is provided as the third lateral-side most inferior point 47a.

As shown in FIG. 4, the third medial-side most inferior point 46a and the third lateral-side most inferior point 47a are provided so as to be closer to the posterior side than the first medial-side most inferior point 36a and the first lateral-side most inferior point 37a provided on the standard-type femoral component 3 are in the anterior-posterior direction. For example, the third medial-side most inferior point 46a and the third lateral-side most inferior point 47a are provided so as to be closer to the posterior side by 1 mm than the first medial-side most inferior point 36a and the first lateral-side most inferior point 37a are. FIG. 4 shows, in an exaggerated manner, the amount of difference of the most inferior points 46a and 47a of the posterior-type femoral component in the anterior-posterior direction, from the most inferior points 36a and 37a of the standard-type femoral component 3.

Configuration of Tibial Plate

As described above, as the tibial plates, there are three types of tibial plates (the anterior-type tibial plate 5, the standard-type tibial plate 6, and the posterior-type tibial plate 7). These three types of tibial plates 5, 6, and 7 have substantially the same configuration except for the positions of the most inferior points in the anterior-posterior direction. Thus, in the description below, the configuration of the standard-type tibial plate 6 will be described first. Subsequently, the configurations of the anterior-type and posterior-type tibial plates 5 and 7 will be described mainly focusing on aspects of the configurations different from those of the standard-type tibial plate 6.

The standard-type tibial plate 6 is made of a synthetic resin or the like. As shown in FIG. 5, the standard-type tibial plate 6 has a plate portion 60 formed substantially in the shape of a flat plate. The plate portion 60 is formed substantially in the shape of an ellipse that is elongated in the left-right direction. The plate portion 60 is provided with a medial recess 61 and a lateral recess 62.

The medial recess 61 is provided as a depression that is in slidable contact with one of the medial condyles 21, 31, and 41 of the femoral components 2, 3, and 4. In the medial recess 61, a face that slides against one of the femur-medial-side sliding faces 26, 36, and 46 of the femoral components 2, 3, and 4 is provided as a tibia-medial-side sliding face 63.

On the other hand, the lateral recess 62 is provided as a depression that is in slidable contact with one of the lateral condyles 22, 32, and 42 of the femoral components 2, 3, and 4. In the lateral recess 62, a face that slides against one of the femur-lateral-side sliding faces 27, 37, and 47 of the femoral components 2, 3, and 4 is provided as a tibia-lateral-side sliding face 64.

On the thus formed sliding faces 63 and 64 described above, the deepest recessed portions are provided as most inferior points 63a and 64a (first distalmost points). The most inferior point 63a provided on the medial-side sliding face 63 is provided as the first medial-side most inferior point 63a, and the most inferior point 64a provided on the lateral-side sliding face 64 is provided as the first lateral-side most inferior point 64a. The first medial-side most inferior point 63a and the first lateral-side most inferior point 64a are positioned on the distalmost side of the tibia 102 in a state where the artificial knee joint implant 1 attached to a patient is extended. The most inferior points 63a and 64a are formed at substantially the middle of the standard-type tibial plate 6 in the anterior-posterior direction, when viewed from a side.

The anterior-posterior positions of the most inferior points provided on the anterior-type tibial plate 5 and the posterior-type tibial plate 7 are different from those of the most inferior points provided on the standard-type tibial plate 6 in the anterior-posterior direction. The other portions have substantially the same shapes.

As shown in FIG. 6, the anterior-type tibial plate 5 also has a medial-side most inferior point 53a (second distalmost point) provided on a tibia-medial-side sliding face 53 of a medial recess 51 and a lateral-side most inferior point 54a (second distalmost point) provided on a tibia-lateral-side sliding face 54 of a lateral recess 52, as in the case of the standard-type tibial plate 6. In the anterior-type tibial plate 5, the medial-side most inferior point 53a is provided as the second medial-side most inferior point 53a, and the lateral-side most inferior point 54a is provided as the second lateral-side most inferior point 54a.

As shown in FIG. 6, the second medial-side most inferior point 53a and the second lateral-side most inferior point 54a are provided so as to be closer to the anterior side than the first medial-side most inferior point 63a and the first lateral-side most inferior point 64a provided on the standard-type tibial plate 6 are in the anterior-posterior direction. For example, the second medial-side most inferior point 53a and the second lateral-side most inferior point 54a are provided so as to be closer to the anterior side by 1 mm than the first medial-side most inferior point 63a and the first lateral-side most inferior point 64a are. FIG. 6 shows, in an exaggerated manner, the amount of difference of the most inferior points 53a and 54a of the anterior-type tibial plate in the anterior-posterior direction, from the most inferior points 63a and 64a of the standard-type tibial plate 6.

On the other hand, as shown in FIG. 7, the posterior-type tibial plate 7 also has a medial-side most inferior point 73a (third distalmost point) provided on a tibia-medial-side sliding face 73 of a medial recess 71 and a lateral-side most inferior point 74a (third distalmost point) provided on a tibia-lateral-side sliding face 74 of a lateral recess 72, as in the case of the standard-type tibial plate 6. In the posterior-type tibial plate 7, the medial-side most inferior point 73a is provided as the third medial-side most inferior point 73a, and the lateral-side most inferior point 74a is provided as the third lateral-side most inferior point 74a.

As shown in FIG. 7, the third medial-side most inferior point 73a and the third lateral-side most inferior point 74a are provided so as to be closer to the posterior side than the first medial-side most inferior point 63a and the first lateral-side most inferior point 64a provided on the standard-type tibial plate 6 are in the anterior-posterior direction. For example, the third medial-side most inferior point 73a and the third lateral-side most inferior point 74a are provided so as to be closer to the posterior side by 1 mm than the first medial-side most inferior point 63a and the first lateral-side most inferior point 64a are. FIG. 7 shows, in an exaggerated manner, the amount of difference of the most inferior points 73a and 74a of the posterior-type tibial plate in the anterior-posterior direction, from the most inferior points 63a and 64a of the standard-type tibial plate 6.

FIG. 8 are views illustrating a difference in the anterior-posterior direction between most inferior points respectively provided on a plurality of types of femoral components and tibial plates. As shown in FIG. 8, the most inferior points 26a and 27a of the anterior-type femoral component 2 shown in FIG. 8B are closer to the anterior side than the most inferior points 36a and 37a of the standard-type femoral component 3 shown in FIG. 8A are. Furthermore, the most inferior points 46a and 47a of the posterior-type femoral component 4 shown in FIG. 8C are closer to the posterior side than the most inferior points 36a and 37a of the standard-type femoral component 3 shown in FIG. 8A are. Furthermore, the most inferior points 53a and 54a of the anterior-type tibial plate 5 shown in FIG. 8E are closer to the anterior side than the most inferior points 63a and 64a of the standard-type tibial plate 6 shown in FIG. 8D are. Furthermore, the most inferior points 73a and 74a of the posterior-type tibial plate 7 shown in FIG. 8F are closer to the posterior side than the most inferior points 63a and 64a of the standard-type tibial plate 6 shown in FIG. 8D are.

Regarding Selection of Femoral Component and Tibial Plate in Surgery

With the artificial knee joint implant 1 according to this embodiment, as described above, one femoral component and one tibial plate are selected from among the plurality of types of femoral components 2, 3, and 4 and tibial plates 5, 6, and 7 according to the shape, the condition, and the like of a knee joint of a patient, and are attached to the patient's knee.

Figure 9A:
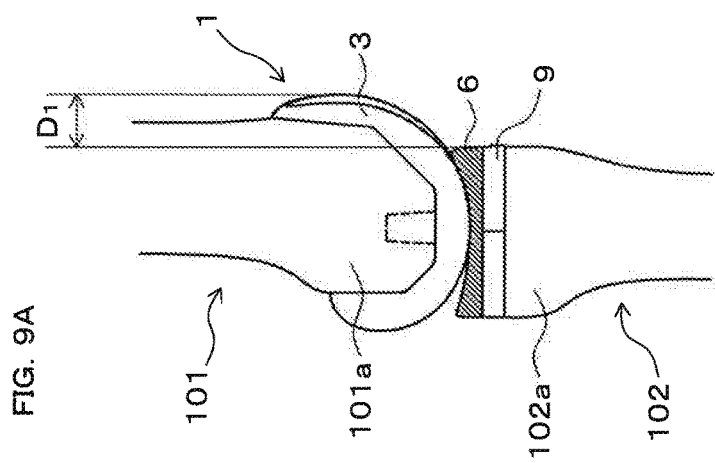

For example, if the surgeon judges that, in order to realize a proper balance between ligaments of a patient, the proper position of the femoral component with respect to the tibial plate in the anterior-posterior direction is a standard position, the surgeon selects a combination that realizes this positional relationship. Specifically, the surgeon selects the standard-type femoral component 3 and the standard-type tibial plate 6, and attaches them to the patient's knee (see FIG. 9A).

If the surgeon judges that, in order to realize a proper balance between ligaments of a patient, the proper position of the femoral component with respect to the tibial plate is an anterior position, the surgeon selects a combination that realizes this positional relationship. Specifically, for example, the surgeon selects the standard-type femoral component 3 and the anterior-type tibial plate 5, and attaches them to the patient's knee.

Figure 9B:
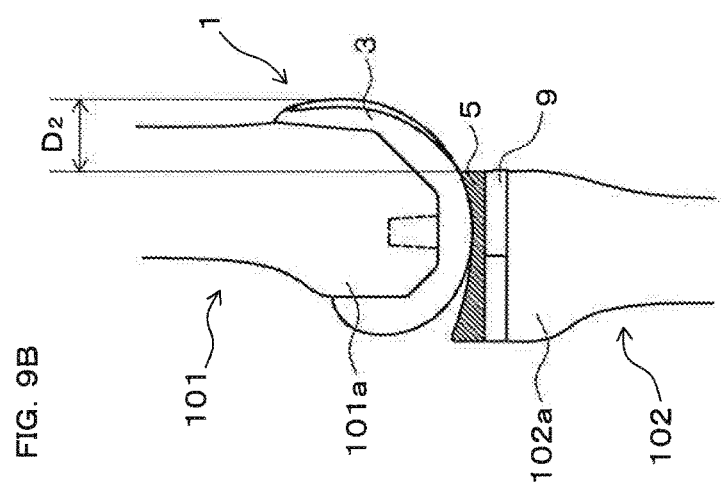

FIG. 9B is a view showing a state in which the standard-type femoral component 3 and the anterior-type tibial plate 5 are attached to a patient's knee. If the standard-type femoral component 3 and the anterior-type tibial plate 5 are combined as shown in FIG. 9B, a protrusion amount $D_2$ in the anterior direction of the anterior end of the femoral component 3 with respect to the anterior end of the tibial plate 5 can be made larger than ($D_1$) in the case of FIG. 9A. That is to say, in the case of FIG. 9B, the femoral component 3 can be positioned closer to the anterior side with respect to the tibial plate 5 than in the case of FIG. 9A.

Although not shown, a combination of the posterior-type femoral component 4 and the standard-type tibial plate 6 or a combination of the posterior-type femoral component 4 and the anterior-type tibial plate 5 also makes it possible for the femoral component to be positioned closer to the anterior side with respect to the tibial plate. In particular, if the posterior-type femoral component 4 and the anterior-type tibial plate 5 are combined, the femoral component can be positioned significantly closer to the anterior side with respect to the tibial plate.

On the other hand, if the surgeon judges that, in order to realize a proper balance between ligaments of a patient, the proper position of the femoral component with respect to the tibial plate is a posterior position, the surgeon selects a combination that realizes this positional relationship. Specifically, for example, the surgeon selects the standard-type femoral component 3 and the posterior-type tibial plate 7, and attaches them to the patient's knee.

Figure 9C:
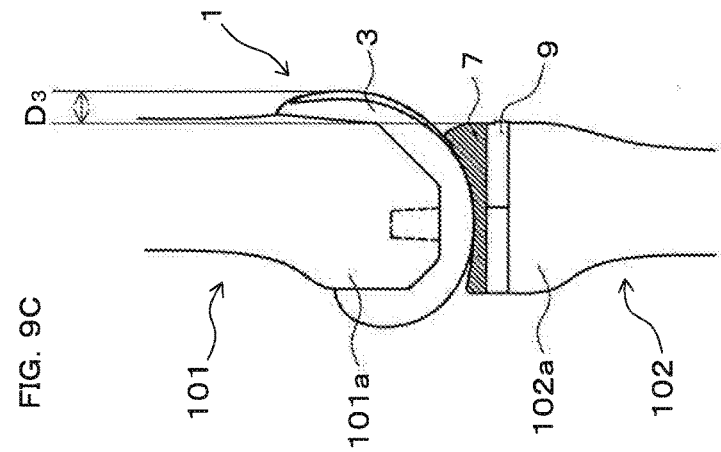

FIG. 9C is a view showing a state in which the standard-type femoral component 3 and the posterior-type tibial plate 7 are attached to a patient's knee. If the standard-type femoral component 3 and the posterior-type tibial plate 7 are combined as shown in FIG. 9C, a protrusion amount $D_3$ in the anterior direction of the anterior end of the femoral component 3 with respect to the anterior end of the tibial plate 7 can be made smaller than ($D_1$) in the case of FIG. 9A. That is to say, in the case of FIG. 9C, the femoral component 3 can be positioned closer to the posterior side with respect to the tibial plate 7 than in the case of FIG. 9A.

Although not shown, a combination of the anterior-type femoral component 2 and the standard-type tibial plate 6 or a combination of the anterior-type femoral component 2 and the posterior-type tibial plate 7 also makes it possible for the femoral component to be positioned closer to the posterior side with respect to the tibial plate. In particular, if the anterior-type femoral component 2 and the posterior-type tibial plate 7 are combined, the femoral component can be positioned significantly closer to the posterior side with respect to the tibial plate.

Effects

As described above, according to the artificial knee joint implant 1 of this embodiment, a surgeon can select one of the plurality of types of tibial plates 5, 6, and 7 according to the shape, the condition, and the like of a knee joint of a patient, and attach that tibial plate to the patient's knee. Accordingly, the contact position of the femoral component and the tibial plate can be adjusted, and, thus, a proper balance between both collateral ligaments can be easily realized.

Thus, according to the artificial knee joint implant 1, it is possible to provide an artificial knee joint implant with which the balance between ligaments can be properly adjusted.

Furthermore, if the plurality of types of tibial plates 5, 6, and 7 respectively having the most inferior points 53a, 54a, 63a, 64a, 73a, and 74a at different positions in the anterior-posterior direction are formed as in the artificial knee joint implant 1, the contact position of the femoral components 2, 3, and 4 and the tibial plates 5, 6, and 7 in the anterior-posterior direction can be adjusted relatively easily.

According to the artificial knee joint implant 1, for example, three tibial plates 5, 6, and 7 can be formed in which the positions of the most inferior points that realize the most proper balance between ligaments of an average patient undergoing artificial knee joint replacement surgery are set to the first most inferior points 63a and 64a, on the anterior side and the posterior side of which the second most inferior points 53a and 54a and the third most inferior points 73a and 74a are set. Accordingly, it is possible to provide an artificial knee joint implant with which the balance between ligaments can be properly adjusted for more patients.

Furthermore, according to the artificial knee joint implant 1, a surgeon can select one of the plurality of types of femoral components 2, 3, and 4 according to the shape, the condition, and the like of a knee joint of a patient, and attach that femoral component to the patient's knee. Accordingly, the contact position of the femoral components 2, 3, and 4 and the tibial plates 5, 6, and 7 can be adjusted, and, thus, a proper balance between both collateral ligaments can be easily realized.

Accordingly, with this configuration, it is possible to provide an artificial knee joint implant with which the balance between ligaments can be properly adjusted.

Furthermore, if the plurality of types of femoral components 2, 3, and 4 respectively having the most inferior points 26a, 27a, 36a, 37a, 46a, and 47a at different positions in the anterior-posterior direction are formed as in the artificial knee joint implant 1, the contact position of the femoral components 2, 3, and 4 and the tibial plates 5, 6, and 7 in the anterior-posterior direction can be adjusted relatively easily.

According to the artificial knee joint implant 1, for example, three femoral components 2, 3, and 4 can be formed in which the positions of the most inferior points that realize the most proper balance between ligaments of an average patient undergoing artificial knee joint replacement surgery are set to the first most inferior points 36a and 37a, on the anterior side and the posterior side of which the second most inferior points 26a and 27a and the third most inferior points 46a and 47a are set. Accordingly, it is possible to provide an artificial knee joint implant 1 with which the balance between ligaments can be properly adjusted for more patients.

In the description above, an embodiment of the present invention was described, but the present invention is not limited thereto, and various modifications may be made within the scope described in the claims. For example, the following modifications are possible.

Figure 10A:
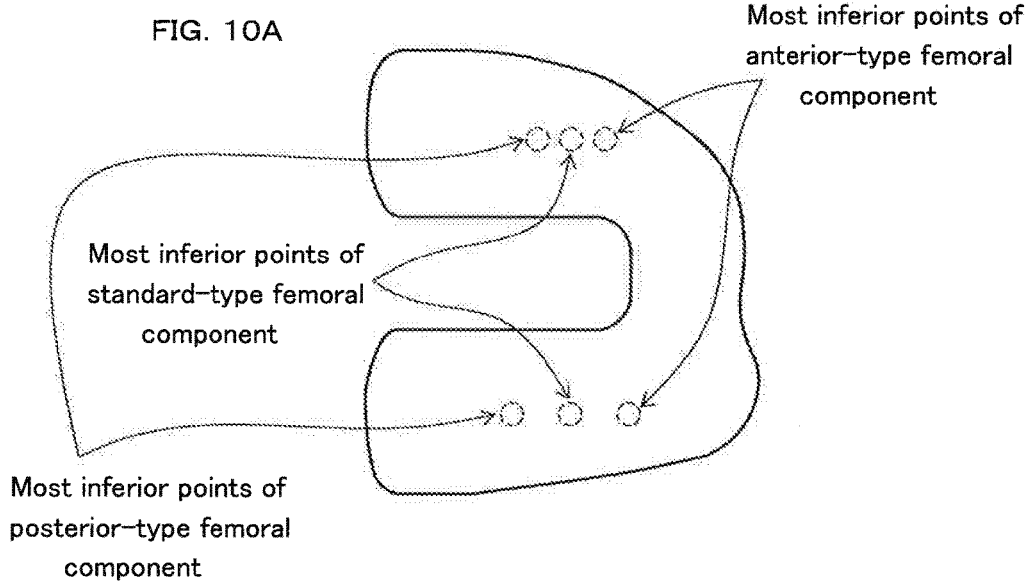
FIG. 10A shows a view illustrating a positional relationship between most inferior points on a medial side and a lateral side respectively provided on a plurality of types of femoral components according to a modified example.
Figure 10B:
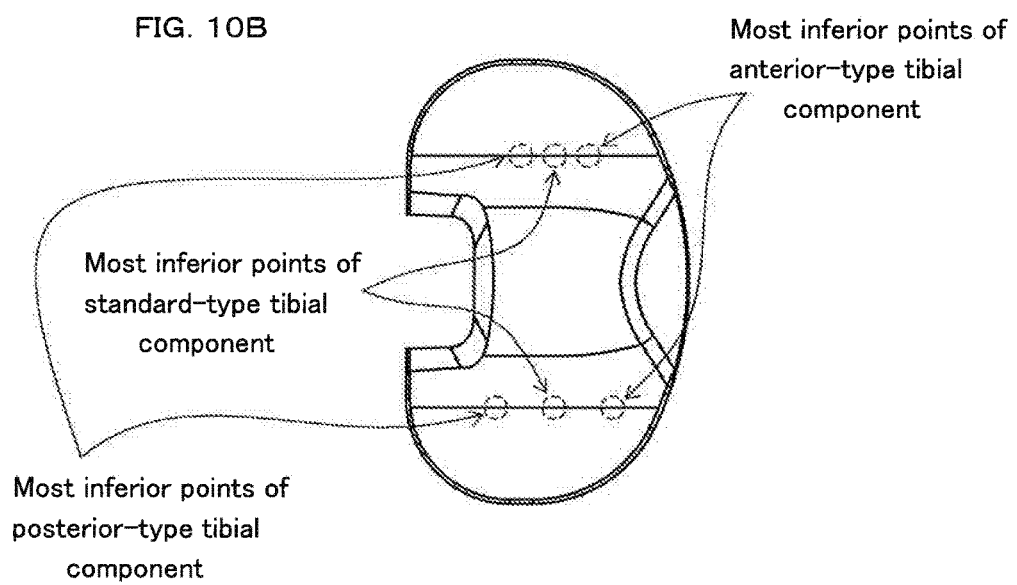
FIG. 10B is a view illustrating a positional relationship between most inferior points on a medial side and a lateral side respectively provided on a plurality of types of tibial plates according to a modified example.

Modified Examples (1) FIG. 10A is a view illustrating a positional relationship between most inferior points on the medial side and the lateral side respectively provided on a plurality of types of femoral components according to a modified example, and FIG. 10B is a view illustrating a positional relationship between most inferior points on the medial side and the lateral side respectively provided on a plurality of types of tibial plates according to the modified example. In the foregoing embodiment, the separation intervals of the medial-side most inferior points 26a, 36a, and 46a in the anterior-posterior direction and the separation intervals of the lateral-side most inferior points 27a, 37a, and 47a in the anterior-posterior direction of the femoral components 2, 3, and 4 are the same (1 mm), but there is no limitation to this. For example, as shown in FIG. 10A, the separation intervals of the medial-side most inferior points in the anterior-posterior direction and the separation intervals of the lateral-side most inferior points in the anterior-posterior direction of the femoral components may be set to be different from each other. Accordingly, the separation intervals of the medial-side most inferior points and the separation intervals of the lateral-side most inferior points in the anterior-posterior direction can be properly set independently, and, thus, it is possible to provide an artificial knee joint implant that fits more patients.

In a similar manner, as shown in FIG. 10B, the separation intervals of the medial-side most inferior points in the anterior-posterior direction and the separation intervals of the lateral-side most inferior points in the anterior-posterior direction of the tibial plates may be set to be different from each other as well. Accordingly, the separation intervals of the medial-side most inferior points and the separation intervals of the lateral-side most inferior points in the anterior-posterior direction can be properly set independently, and, thus, it is possible to provide an artificial knee joint implant that fits more patients.

(2) In the foregoing embodiment, the plurality of types of tibial plates 5, 6, and 7 are provided with the most inferior points 53a, 54a, 63a, 64a, 73a, and 74a, but there is no limitation to this. That is to say, even if the tibial plates do not have most inferior points at different anterior-posterior positions, it is sufficient that the tibial plates respectively have at least either tibia-side sliding faces at different positions with respect to the tibia in a state where the tibial plates are fixed to the tibia, or tibia-side sliding faces in different shapes.

Figure 11A:
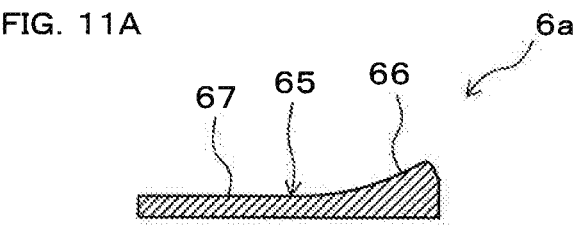
FIG. 11 shows cross-sectional views showing shapes of a plurality of types of tibial plates according to a modified example.
Figure 11B:
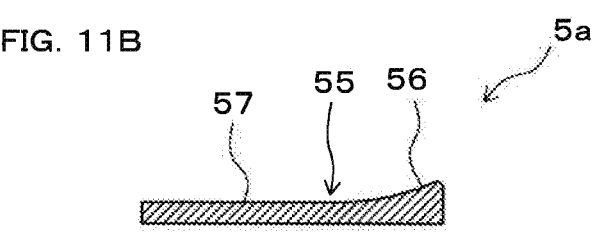
Figure 11C:
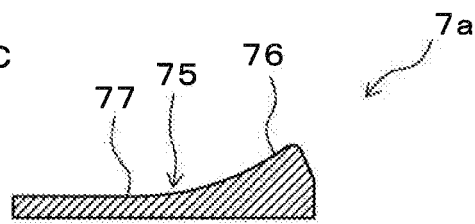

FIGS. 11A, 11B, and 11C are cross-sectional views showing a plurality of types of first to third tibial plates 5a, 6a, and 7a according to a modified example. As shown in FIG. 11, the tibial plates 5a, 6a, and 7a have tibia-side sliding faces 55, 65, and 75, and the tibia-side sliding faces 55, 65, and 75 respectively have inclined faces 56, 66, and 76 formed on the anterior side and flat faces 57, 67, and 77 formed on the posterior side.

The plurality of types of tibial plates 5a, 6a, 7a according to this modified example are provided with the inclined faces 56, 66, and 76 that have different lengths in the anterior-posterior direction. Specifically, the second tibial plate 5a is provided with the inclined face 56 that has the shortest length in the anterior-posterior direction, and the third tibial plate 7a is provided with the inclined face 76 that has the longest length in the anterior-posterior direction. In this manner, even in the case of components (tibial plates in this modified example) having no most inferior points, if a plurality of types of such components are formed as in this modified example, the contact position with the corresponding component can be adjusted. Accordingly, as in the foregoing embodiment, it is possible to provide an artificial knee joint implant with which the balance between ligaments can be properly adjusted.

(3) In the foregoing embodiment, an application example of the present invention was described using a CR-type artificial knee joint as an example, but there is no limitation to this, and application to other types of artificial knee joints is also possible. Specifically, for example, application to a PS (posterior stabilizing)-type artificial knee joint, a CS (cruciate substituting)-type artificial knee joint, a CCK (constrained condylar knee)-type artificial knee joint, and the like is also possible.

Figure 12A:
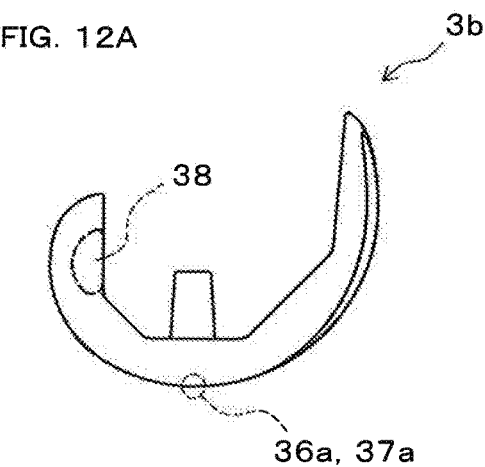
Figure 12B:
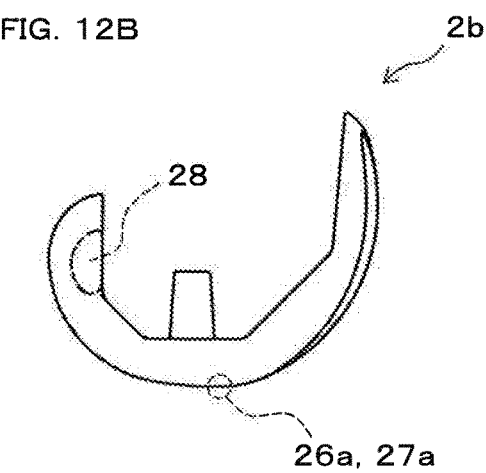
Figure 12C:
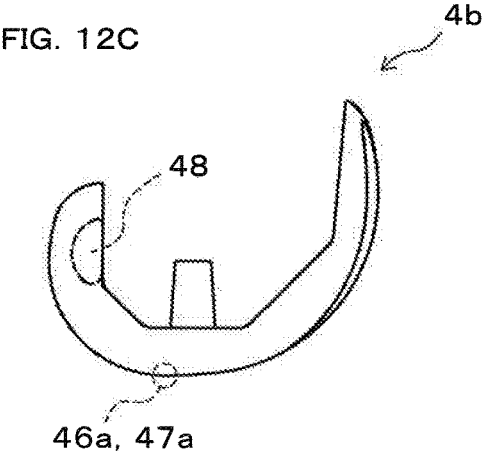
Figure 12D:
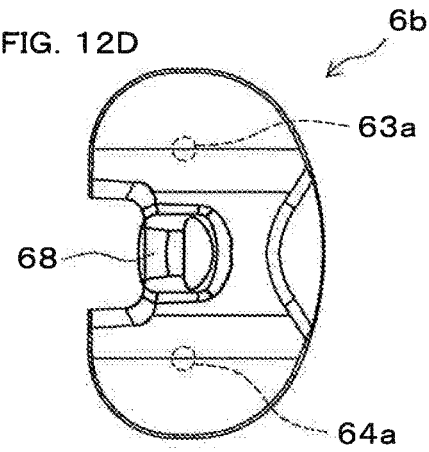
Figure 12E:
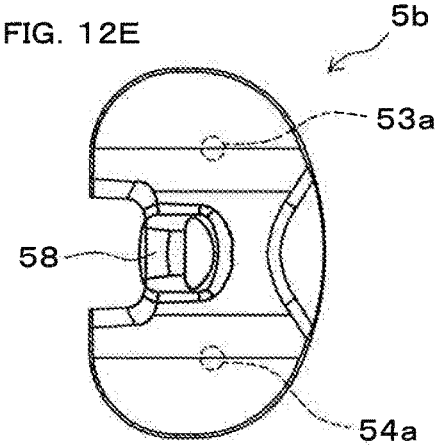
Figure 12F:
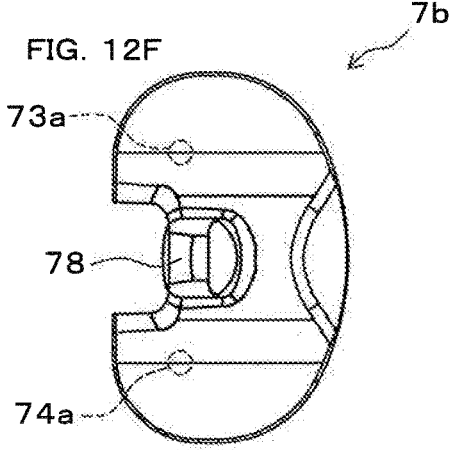

FIG. 12 shows views illustrating shapes of a femoral component and a tibial plate in the case where the present invention is applied to a PS-type artificial knee joint, wherein FIGS. 12A to 12C are views of a femoral component, and FIGS. 12D to 12F are views of a tibial plate. Specifically, FIG. 12A is a view of a most inferior point standard-type femoral component 3b, FIG. 12B is a view of a most inferior point anterior-type femoral component 2b, and FIG. 12C is a view of a most inferior point posterior-type femoral component 4b. Furthermore, FIG. 12D is a view of a most inferior point standard-type tibial plate 6b, FIG. 12E is a view of a most inferior point anterior-type tibial plate 5b, and FIG. 12F is a view of a most inferior point posterior-type tibial plate 7b.

In the case of the artificial knee joint implant according to this modified example, the femoral components 2b, 3b, and 4b are respectively provided with cams 28, 38, and 48, and the tibial plates 5b, 6b, and 7b are respectively provided with posts 58, 68, and 78. The artificial knee joint implant according to this modified example is configured such that, when the flexion angle of the knee is a predetermined angle or more, one of the cams 28, 38, and 48 and one of the posts 58, 68, and 78 are brought into contact with each other to guide the flexion movement of the knee.

As in the foregoing embodiment, according to the PS-type artificial knee joint implant of this modified example, the plurality of types of femoral components 2b, 3b, and 4b respectively have the most inferior points at different positions in the anterior-posterior direction. Furthermore, the plurality of types of tibial plates 5b, 6b, and 7b respectively have the most inferior points at different positions in the anterior-posterior direction. Accordingly, as in the foregoing embodiment, it is possible to provide an artificial knee joint implant with which the balance between ligaments can be properly adjusted.

(4) In the foregoing embodiment, the artificial knee joint implant 1 is provided with the plurality of types of femoral components 2, 3, and 4 and the plurality of types of tibial plates 5, 6, and 7, but there is no limitation to this, and the artificial knee joint implant 1 may be provided with a plurality of types of femoral components and one tibial plate or a plurality of types of tibial plates and one femoral component.

The present invention is widely applicable as an artificial knee joint implant including a femoral component and a tibial plate.

The invention claimed is:

1. An artificial knee joint implant, comprising a femoral component and a tibial plate,
wherein the tibial plate has a tibia-side sliding face that slides against the femoral component, and
the tibial plate of the artificial knee joint implant comprises one of a plurality of tibial plate types respectively having at least either the tibia-side sliding faces at different positions with respect to a tibia in a state where the tibial plate types are fixed to a tibial tray attached to the tibia, or the tibia-side sliding faces in different shapes, and wherein the tibia-side sliding faces are respectively provided with distalmost points positioned on a distalmost side in an extension direction, which is a direction in which the artificial knee joint implant that is fixed to a femur and the tibia is extended, and each of the plurality of tibial plate types has the distalmost point whose position with respect to a knee joint is different from the positions of the distalmost points of the other tibial plate types in an anterior-posterior direction in a state where each of the plurality of tibial plate types are fixed to the tibial tray.

2. The artificial knee joint implant according to claim 1, wherein the distalmost points include a first distalmost point, a second distalmost point, and a third distalmost point respectively corresponding to the plurality of tibial plate types, and the plurality of tibial plate types include a first tibial plate type provided with the first distalmost point that is at a predetermined position in the anterior-posterior direction, a second tibial plate type provided with the second distalmost point that is closer to an anterior side than the first distalmost point is in the anterior-posterior direction, and a third tibial plate type provided with the third distalmost point that is closer to a posterior side than the first distalmost point is in the anterior-posterior direction.

3. The artificial knee joint implant according to claim 2, wherein the first tibial plate type is provided with a first medial-side distalmost point and a first lateral-side distalmost point as two first distalmost points that are spaced away from each other in a left-right direction, the second tibial plate type is provided with a second medial-side distalmost point and a second lateral-side distalmost point as two second distalmost points that are spaced away from each other in the left-right direction, the third tibial plate type is provided with a third medial-side distalmost point and a third lateral-side distalmost point as two third distalmost points that are spaced away from each other in the left-right direction, and separation intervals of the medial-side distalmost points in the anterior-posterior direction and separation intervals of the lateral-side distalmost points in the anterior-posterior direction are different from each other.

4. An artificial knee joint implant, comprising a femoral component and a tibial plate, wherein the femoral component has a femur-side sliding face that slides over the tibial plate, and the femoral component of the artificial knee joint implant comprises one of a plurality of femoral component types respectively having at least either the femur-side sliding faces at different positions with respect to a femur in a state where the femoral component types are fixed to the femur, or the femur-side sliding faces in different shapes, and wherein the femur-side sliding faces are respectively provided with distalmost points positioned on a distalmost side in an extension direction, which is a direction in which the artificial knee joint implant that is fixed to the femur and a tibia is extended, and each of the plurality of femoral component types has the distalmost point whose position with respect to a knee joint is different from the positions of the distalmost points of the other femoral component types in an anterior-posterior direction in a state where each of the plurality of femoral component types are fixed to the femur.

5. The artificial knee joint implant according to claim 4, wherein the distalmost points include a first distalmost point, a second distalmost point, and a third distalmost point respectively corresponding to the plurality of types of femoral component types and the plurality of femoral component types include a first femoral component type provided with the first distalmost point that is at a predetermined position in the anterior-posterior direction, a second femoral component type provided with the second distalmost point that is closer to an anterior side than the first distalmost point is in the anterior-posterior direction, and a third femoral component type provided with the third distalmost point that is closer to a posterior side than the first distalmost point is in the anterior-posterior direction.

6. The artificial knee joint implant according to claim 5, wherein the first femoral component type is provided with a first medial-side distalmost point and a first lateral-side distalmost point as two first distalmost points that are spaced away from each other in a left-right direction, the second femoral component type is provided with a second medial-side distalmost point and a second lateral-side distalmost point as two second distalmost points that are spaced away from each other in the left-right direction, the third femoral component type is provided with a third medial-side distalmost point and a third lateral-side distalmost point as two third distalmost points that are spaced away from each other in the left-right direction, and separation intervals of the medial-side distalmost points in the anterior-posterior direction and separation intervals of the lateral-side distalmost points in the anterior-posterior direction are different from each other.

7. An artificial knee joint implant, comprising a femoral component and a tibial plate, wherein the tibial plate has a tibia-side sliding face that slides against the femoral component, the artificial knee joint implant comprises a plurality of tibial plate types respectively having at least either the tibia-side sliding faces at different positions with respect to a tibia in a state where the tibial plate types are fixed to a tibial tray attached to the tibia, or the tibia-side sliding faces in different shapes, the tibia-side sliding faces respectively have inclined faces formed on an anterior side and flat faces formed on a posterior side, and the plurality of types of tibial plate types are provided with the inclined faces that have different lengths in an anterior-posterior direction.

* * * * *